(12) United States Patent
Rovati et al.

(10) Patent No.: US 7,482,371 B2
(45) Date of Patent: Jan. 27, 2009

(54) N-PHENYLBENZAMIDE DERIVATIVES AS DRUGS FOR THE TREATMENT OF COPD

(75) Inventors: Lucio Claudio Rovati, Monza (IT); Antonio Giordani, Pavia (IT); Gianfranco Caselli, Milan (IT)

(73) Assignee: Rottapharm S.p.A., Milan (IT)

( * ) Notice: Subject to any disclaimer, the term of this patent is extended or adjusted under 35 U.S.C. 154(b) by 0 days.

(21) Appl. No.: 11/206,803

(22) Filed: Aug. 19, 2005

(65) Prior Publication Data

US 2006/0052427 A1 Mar. 9, 2006

(30) Foreign Application Priority Data

Aug. 19, 2004 (EP) ................... 04019648

(51) Int. Cl.
*C11D 3/00* (2006.01)

(52) U.S. Cl. ............... 514/381; 514/369; 514/318

(58) Field of Classification Search ........... 514/183
See application file for complete search history.

(56) References Cited

U.S. PATENT DOCUMENTS 5,976,576 A 11/1999 Makovec et al.
2003/0149029 A1* 8/2003 McKew et al. ........... 514/227.8

FOREIGN PATENT DOCUMENTS

| EP | 0 896 821 A1 | 2/1999 |
| WO | WO 90/09989 A | 9/1990 |
| WO | WO 00/33831 A1 | 6/2000 |
| WO | WO 2005/123071 | * 12/2005 |

OTHER PUBLICATIONS

D'Amato et al. Pharmacokinetics of Andolast after Administration of Single Escalating Doses by Inhalation in Mild Asthmatic Patients Biopharmaceutics & Drug Disposition 22:73-81 (2001).*
L. Revel et al.: "CR 2039, a new bis-(1H-tetrazol-5-yl)ohenylbenzamide derivative with potential for the topical treatment of asthma." European Journal of Pharmacology. Dec. 8, 1992, vol. 229, No. 1, pp. 45-53, XP002305101, ISSN: 0014-2999.
F. Makovec et al.: "Antiallergic and Cytoprotective Activity of New N-phenylbenzamido acid derivatives." Journal of MEdicial Chemistry. Oct. 2, 1992, vol. 35, No. 20, pp. 3633-3640, XP002305102, ISSN: 0022-2623.

S. Persiani et al.: "Pharmacokinetics of Andolast after Administration of Single Escalating Doses by Inhalation in Mild Asthmatic Patients." Biopharmaceutics & Drug Disposition. Mar. 2001, vol. 22, No. 2, Mar. 2001, pp. 73-81, XP008038661.
P.M. O'Byrne et al.: "The Many Faces of Airway Inflammation. Asthma and Chronic Obstructive Pulmonary Disease" American Journal of Respiratory and Critical Care Medicine, American Lung Association, New York, NY, US, vol. 159, No. 5, 1999, pp. 541-566, XP000911062, ISSN: 1073-449X.
M. D. Bhattarai: "Asthma Mistaken for Chronic Obstructive Pulmonary Disease", The Lancet, Lancet Ltd., London, GB, vol. 361, No. 9372, May 31, 2003, pp. 1914-1915, XP004428411, ISSN: 0140-6736.

* cited by examiner

*Primary Examiner*—James O Wilson
*Assistant Examiner*—Timothy E Betton
(74) *Attorney, Agent, or Firm*—Sughrue Mion, PLLC

(57) ABSTRACT

The invention relates to the use of a pharmaceutically active derivative of N-phenylbenzamide of Formula (I) or of a pharmaceutically acceptable salt thereof, for preparing a medicament for the therapeutic treatment of Chronic Obstructive Pulmonary Disease (COPD).

Compounds of Formula (I):

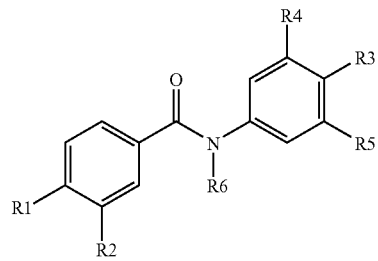

wherein $R_1$ is cyano, nitro, halogen, hydroxy, $C_1$-$C_4$ alkyl, methoxy or tetrazol-5-yl group, $R_2$ is hydrogen, hydroxy or methoxy, $R_3$ is a tetrazol-5-yl group or hydrogen, $R_4$ and $R_5$ are hydrogen if $R_3$ is tetrazol-5-yl group, or $R_4$ and $R_5$ are independently selected from the group consisting of carboxy, methoxycarbonyl, ethoxycarbonyl and carbamoyl if $R_3$ is hydrogen, and $R_6$ is hydrogen or methyl.

3 Claims, 3 Drawing Sheets

N-PHENYLBENZAMIDE DERIVATIVES AS DRUGS FOR THE TREATMENT OF COPD

BACKGROUND OF THE INVENTION

The present invention relates to the use of pharmaceutically active derivatives of N-phenylbenzamide for the preparation of a medicament for the treatment of Chronic Obstructive Pulmonary Disease (COPD).

COPD is a major and growing global health problem, it is predicted to become the fifth most common cause of disability in the world by 2020, and it is an increasingly common cause of hospital admission as well. The lack of effective therapeutic agents for treating this disease prompted a lot of efforts within the scientific community in order to identify appropriate pharmacological agents able to satisfactorily address this disease.

Based on current knowledge (*National Institute of Health, National Heart, Lung and Blood Institute: GOLD, Global Initiative for Chronic Obstructive Lung Disease: Global Strategy for Diagnosis, Management and Prevention of Chronic Obstructive Pulmonary Disease*; update 2003), COPD is a disease state characterized by airflow limitation that is not fully reversible. The airflow limitation is usually both progressive and associated with an abnormal inflammatory response of the lungs to noxious particles or gases, most often related to cigarette smoking. Symptoms, functional abnormalities and complications of COPD can all be explained on the basis on this underlying inflammation and the resulting pathology. The chronic airflow limitation characteristic of COPD is caused by a mixture of small airway disease (obstructive bronchiolitis) and parenchymal destruction (emphysema), the relative contributions of which vary from the person to person. Chronic inflammation causes remodelling and narrowing of the small airways. Destruction of the lung parenchyma, also by inflammatory processes, leads to the loss of alveolar attachments to the small airways and decreases lung elastic recoil; in turn, these changes diminish the ability of the airways to remain open during expiration. The terms "emphysema" and "chronic bronchitis" are frequently used clinically and included in the definition of COPD. Emphysema, or destruction of the gas-exchanging surfaces of the lung (alveoli), describes one of several structural abnormalities present in patients with COPD. Chronic bronchitis, or the presence of cough and sputum production for at least 3 months in each of two consecutive years, remains a clinically and epidemiologically useful term. However, it does not reflect the major impact of airflow limitation on morbidity and mortality in COPD patients. Therefore, the term COPD correctly defines this disease overall.

As anticipated above, COPD is delineated by chronic inflammation throughout the airways, parenchyma, and pulmonary vasculature. The intensity as well as the cellular and molecular characteristics of the inflammation vary as the disease progresses. Over time, inflammation damages the lungs and leads to the pathologic changes characteristic of COPD (Sutherland E. R. et al. *Management of Chronic Obstructive Pulmonary Disease. N. Engl. J. Med.* 2004; 350: 2689-97; Hogg J. C. et al. *The nature of small-airway obstruction in Chronic Obstructive Pulmonary Disease. N. Engl. J. Med.* 2004;350: 2645-53).

In fact, COPD is characterised by an increase in neutrophils, macrophages, and T lymphocytes (especially CD8[+]) in various parts of the lungs. There may also be an increase in eosinophils in some patients, particularly during exacerbations. These increases are brought about by increases in inflammatory cell recruitment, survival, and/or activation. Many studies reveal a correlation between the number of inflammatory cells of various types in the lung and the severity of COPD.

Pharmacological therapy is used to prevent and control symptoms, reduce the frequency and severity of exacerbations, improve health status, and improve exercise tolerance. Therefore, treatment of COPD heavily depends on anti-inflammatory and bronchodilator drugs.

None of the existing medications for COPD have been shown to modify the long-term decline in lung function that is the hallmark of this disease.

The previous International Patent application WO 90/09989 from our group, refers to N-phenylbenzamide derivatives of Formula (I):

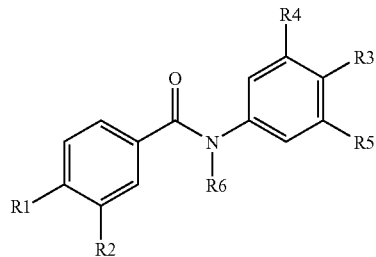

where $R_1$ is cyano, nitro, halogen, hydroxy, $C_1$-$C_4$ alkyl, methoxy or tetrazol-5-yl group, $R_2$ is hydrogen, hydroxy or methoxy, $R_3$ is a tetrazol-5-yl group or hydrogen, $R_4$ and $R_5$ are hydrogen if $R_3$ is tetrazol-5-yl group, or $R_4$ and $R_5$ are independently selected from the group consisting of carboxy, methoxycarbonyl, ethoxycarbonyl and carbamoyl if $R_3$ is hydrogen, and $R_6$ is hydrogen or methyl.

These compounds have been claimed in WO 90/09989 for controlling gastric secretion and as protective agents for gastro-enteric mucous membrane.

Finally, compounds of formula (I) have been mentioned as suitable agents for pharmacological treatment of various conditions which can be attributed to hypersensitivity to allergens, such as bronchial asthma, allergic rhinitis, and conjunctivitis.

Among compounds of Formula (I), the derivative of formula (Ia), [N-4-(1H-tetrazol-5-yl)phenyl-4-(1H-tetrazol-5-yl)benzamide], Andolast, CR2039, in which $R_2$, $R_4$, $R_5$ and $R_6$ are hydrogen and $R_1$ and $R_3$ are tetrazol-5-yl groups, was found endowed with pharmacological properties particularly promising for the treatment of asthma (Revel L. et al. *CR 2039, a new bis-(1H-tetrazol-5-yl)phenylbenzamide derivative with potential for the topical treatment of asthma. Eur. J. Pharmacol.* 1992; 229: 45-53). Suitable pharmaceutical formulations for the use of compound (Ia) in the treatment of asthma have been described in U.S. Pat. No. 5,976,576.

Compound of Formula (Ia) (Andolast, CR2039):

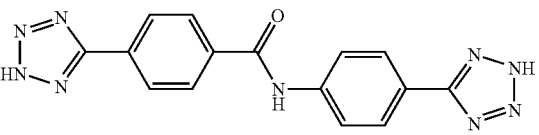

Asthma is the other major chronic obstructive disease of the airways characterised by an underlying airway inflammation. Asthma and COPD have their major symptoms in common, but these are generally more variable in asthma than in COPD. In addition, airflow limitation in asthma is most often completely reversible, either spontaneously or with treatment, while in COPD it is never fully reversible and is usually progressive if exposure to noxius agents continues. In asthma, there is also more evidence of airway hyperresponsiveness (AHR), i.e. of an abnormal bronchoconstrictor response to stimuli.

The underlying chronic airway inflammation is also very different: that in asthma is mainly eosinophilic and driven by $CD4^+$ T lymphocytes, particularly of the Th2 subpopulation, which release a family of proinflammatory cytokines including IL-4, IL-5 and IL-13. Conversely, the chronic inflammation in COPD is neutrophilic and characterised by the presence of increased numbers of macrophages and $CD8^+$ T lymphocytes.

Finally, the responses to treatment of asthma and COPD are dramatically different. Despite the major chronic inflammatory component in both conditions, corticosteroids are significantly more effective in asthma than in COPD, the latter being more sensitive to bronchodilators such as β2 adrenergic agonists and anticholinergics.

The limited value of corticosteroids in reducing inflammation in COPD suggests that novel types of nonsteroidal anti-inflammatory treatment may be needed. There are several new approaches to anti-inflammatory treatment in COPD including, for example, phosphodiesterase inhibitors, transcription factor $NF_{-K}B$ inhibitors, adhesion molecule blockers, matrix metalloproteinase inhibitors, and potassium ($K^+$) channel openers. The latter have several characteristics that will be beneficial in COPD, as it will be described below.

The pharmacological activity of compounds of formula (I) and particularly of compound (Ia) was thought to be mainly due to anti-allergic proprieties of this class of compounds which have been proved to block histamine release (Makovec F. et al. *Antiallergic and cytoprotective activity of new N-phenylbenzamido acid derivatives. J. Med. Chem.* 1992; 35:3633-40), hence their clinical indication for allergic rhinitis and asthma treatment.

Unexpected pharmacological findings now indicate that compounds of Formula (I) as defined above and in particular compound (Ia), Andolast, relieve the different components of the airways inflammatory response, acting through a previously not identified mechanism.

In fact, Andolast decreases both antibody-mediated and cell-mediated inflammatory responses in atopic subjects.

With respect to the former, Andolast has shown a potent inhibitory effect on IL-4 dependent IgE synthesis by human B lymphocytes from allergic donors. This effect leads to the decrease in allergen-triggered mast cell sensitisation and consequently to the inhibition of IgE-dependent mediator release, including histamine, which is responsible for airway inflammation and AHR in atopic bronchial asthma.

With respect to cell-mediated processes, data from atopic mild-moderate asthmatic patients indicated that a standard treatment course with Andolast is able to induce an inhibitory effect on T lymphocytes (Th2) production of the eosinophil recruiter cytokine IL-5, with a consequent decrease in the percentage of eosinophils in the sputum. Since these cell-mediated processes are effective in both atopic and non-atopic subjects, this effect may contribute to the decrease in airway inflammation and AHR in both kind of patients.

In accordance with the present invention, it has now been surprisingly found that compounds of Formula (I) as defined above are endowed with excellent activity in the activation of calcium ($Ca^{2+}$)-dependent $K^+$ channels, thus highlighting these compounds as unexpectedly suitable pharmacological agents particularly for the treatment of COPD, as it will be detailed below.

SUMMARY OF THE INVENTION

Thus, one aspect of the present invention is the use of a compound of Formula (I) as defined above for the preparation of a medicament for the treatment of COPD.

DESCRIPTION OF THE INVENTION

Figure 1:
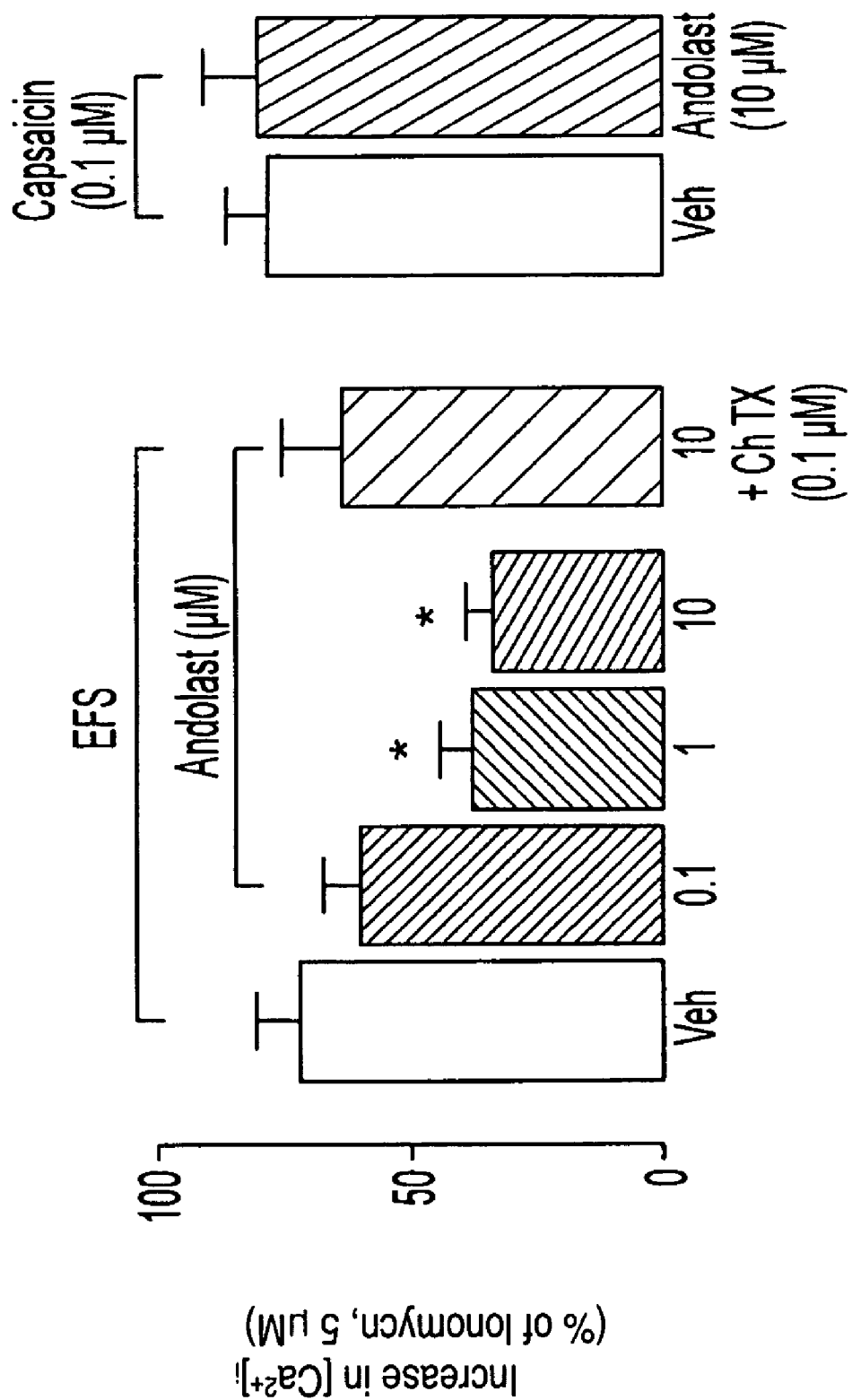
FIG. 1 illustrates the effect of Andolast in inhibiting $[Ca^{2+}]i$ mobilization induced by EFS (40 mA/cm$^2$, 1 msec pulse duration, for 10 sec) in newborn rat cultured DRG neurons, but not that induced by capsaicin (0.1 μM). The effect of Andolast on EFS is reverted by 0.1 μM charybdotoxin (ChTX).

Preferred compounds for use in the present invention are compounds of Formula (I) as defined above in which $R_1$ is a tetrazol-5-yl group. A particularly preferred compound is the compound (Ia), in which $R_2$, $R_4$, $R_5$ and $R_6$ are hydrogen and and $R_3$ are tetrazol-5-yl groups.

The above-mentioned $K^+$ channel opening properties have been shown in experiments that will be reported in the detailed description of the invention. In these experiments, Andolast was able to inhibit the activation of vagal primary sensory neurons (as determined by the inhibition of intracellular $Ca^{2+}$ mobilization stimulated by depolarizing electric stimuli, EFS), to inhibit the so-called neurogenic inflammation in the airways which is derived by the neural release of tachykinins and calcitonin gene-related peptide (CGRP), and the consequent bronchoconstriction. These effects are completely abolished by the selective high-conductance $Ca^{2+}$-activated $K^+$ channel inhibitor charybdotoxin, thus proving that these pharmacological effects are mediated by the opening of these $K^+$ channels.

Ion channels are transmembrane proteins, which catalyse the transport of inorganic ions across cell membrane. $K^+$ channels represent the largest and most diverse group of ion channels. The activity of $K^+$ channels significantly contributes to generation of resting membrane potential and repolarizing/hyperpolarizing currents in a wide variety of cell types. Airway smooth muscle and nerves express $K^+$ channels which are involved in the regulation of contractile activity and neural reflexes at this level. At least three types of such channels are present in the airway, namely $Ca^{2+}$-activated, delayed-rectifier voltage-dependent, and ATP-sensitive $K^+$ channels.

$Ca^{2+}$-activated $K^+$ ($K_{ca}$) channels differ from most of the other $K^+$ channels in that their activation is under dual control, since they are activated either by intracellular $Ca^{2+}$ concentration increase or membrane depolarisation.

$K_{Ca}$ channels are further subclassified into three principal groups on the basis of their biophysical characteristics of single channel conductance: small conductance ($SK_{Ca}$) intermediate conductance ($IK_{Ca}$), and big (high) conductance ($BK_{Ca}$). Though within these subgroups $BK_{Ca}$ are the most studied, some recent works address $SK_{Ca}$ and $IK_{Ca}$ pharmacological properties (Jensen B. S. et al; WO 00/33834, 15 Jun. 2000; Use of isatin derivatives as ion channel activating agents).

In airway smooth muscle (ASM) cells, $BK_{Ca}$ channels activate a negative feedback mechanism by which the actions of depolarizing stimuli and/or $Ca^{2+}$ mobilizing agents are antagonised or terminated as a result of the hyperpolarization produced by outward $K^+$ movements that restore the electrical stability of the cell membrane.

As anticipated above, many in vitro and in vivo studies, performed in both animals and humans, have shown that $K^+$ channel openers are able to induce hyperpolarization of ASM cells, bronchodilation, suppression of airway hyperresponsiveness (AHR), and inhibition of neural reflexes.

With respect to this last point, it is important to note that there is a close interaction between airway nerves and inflammation. Many inflammatory mediators may modulate cholinergic and sensory nerves in the airways through the activation of receptors on nerve terminals (Barnes P. J. *Modulation of neurotransmission in airways. Physiol. Rev.* 1992; 72: 699-729). Sensory nerves mainly release neuropeptides, such as the tachychinins (e.g. substance P, SP, and neurokinin A, NKA) and CGRP. When released from central endings, they are associated with pain transmission and with the activation of protective reflexes (e.g. cough) However, sensory nerves in turn may also amplify inflammation in the airways when activated by mechanical and chemical stimuli (e.g. cigarette smoke), generating antidromic impulses and a local axon reflex that releases the same neuropeptides from peripheral endings, leading to an excitatory nonadrenergic noncholinergic (eNANC) contraction and to neurogenic inflammation. This neurogenic inflammation is described in many organs, and has been documented in the upper and lower respiratory tract in several species (Barnes P. J. *NANC nerves and neuropeptides.* In: Barnes P. J., Rogers I. W., Thomson N. C. (Eds.) 1998, Academic Press, London, 423-58; Maggi C. A. et al. *Neuropeptides as regulators of airway function: vasoactive intestinal peptide and the tachykinins. Physiol. Rev.* 1995; 75: 277-322). In fact, besides smooth muscle contraction and thus direct bronchoconstriction, these neuropeptides induce a series of inflammatory responses that include stimulation of submucosal gland secretion, vasodilatation, increase in vascular permeability, stimulation of mast cells, stimulation of B and T lymphocytes, stimulation of macrophages, chemoattraction of eosinophils and neutrophils, and the vascular adhesion of neutrophils. The idea that sensory nerves may amplify and spread the inflammatory response has attracted considerable attention as it may contribute to the inflammation in airway disease, such as asthma and COPD (Joos G F et al. *The role of neural inflammation in asthma and Chronic Obstructive Pulmonary Disease.* Ann. N.Y. Acad. Sci. 2003; 992: 218-30). Tachykinins also enhance cholinergic neurotransmission by facilitating acetylcholine release at cholinergic nerve terminals and by enhancing ganglionic transmission (Watson N. et al. *Endogenous tachykinins facilitate transmission through parasympathetic ganglia in guinea pig trachea. Br. J. Pharmacol.* 1993; 109: 751-59).

Of at least similar importance with regard to the role of airway nerves in the pathogenesis of COPD is the fact that the major reversible component of airway narrowing in COPD is an increased cholinergic bronchomotor tone, which otherwise constitutes only one of the many factors contributing to bronchial obstruction in asthma. Hence, anticholinergics are even more effective than β2 adrenergic agonists in COPD patients. It has been suggested that COPD patients could benefit from the pharmacological properties of $K^+$ channel openers, that are able to impair ganglionic transmission in the vagus nerve and to reduce acetylcholine release from nerve terminals. The modulatory effects of these drugs on cholinergic neurotransmission, due to neural hyperpolarization, are confirmed by their greater inhibitory action exerted in guineapigs against bronchoconstriction induced by vagal stimulation, in comparison with that elicited by intravenous infusion of acetylcholine.

The relaxant properties of $BK_{Ca}$ activating agents in the airway smooth muscle, along with the involvement of these channels in the release of several inflammatory mediators and in neural transmission, suggest COPD as a promising target for pharmacological agents acting as $K_{Ca}$ channels openers (G. Pelaia et al. *Potential role of potassium channel openers in the treatment of asthma and Chronic Obstructive Pulmonary Disease. Life Sci.* 2002;70: 977-90).

It should be pointed out that other $K^+$ channels openers, e.g. Cromakalim, indeed have been proved to significantly inhibit experimentally induced bronchoconstriction in animal models, and clinical trials proved Cromakalim to be effective in chronic airway inflammation. However, this drug as well its congeners Lemakalim and Bimakalim act on another type of $K^+$ channel, the ATP sensitive $K^+$ channel, $K_{ATP}$, which is a different $K^+$ channel from $BK_{Ca}$. $K_{ATP}$ channel openers have been proved to be powerful relaxant of vascular smooth muscle and their use is therefore limited by unwanted side effects such as hypotension. In addition, activators of this channel lack inhibitory properties in inflammatory mediator release and inhibition of inflammatory cell recruitment into the airways, that has been suggested as a key component for COPD treatment. Conversely, these properties have been demonstrated for Andolast that is not only effective on neurogenic inflammation through activation of $BK_{Ca}$ channels, but also decreases the antibody-mediated and the cell-mediated inflammatory responses. Since $K^+$ channels are expressed by several inflammatory and immune cells such as T lymphocytes, neutrophils, basophils and macrophages involved in airway chronic inflammation, it has been proposed that these channels may possibly contribute to modulate different airway inflammatory responses. As a consequence, opening of $K^+$ channels demonstrated here may explain the mechanism of action of Andolast also in this respect, that would therefore support its overall, airway specific, anti-inflammatory properties and inhibitory effects on inflammatory cell recruitment (possibly including neutrophils and macrophages that are characteristic of COPD inflammation) by modulating the release of different chemokines and cytokines.

Taken together all these evidences support the use of derivatives of formula (I) and particularly of compound of formula (Ia), Andolast, for the preparation of a medicament for the treatment of COPD, based on the unexpected findings described here.

Effect of Andolast On Neurogenic Inflammation and Demonstration of $K_{Ca}$ Channel Involvement Specific studies have been conducted to demonstrate that:

a) Andolast inhibits mobilization of intracellular $Ca^{2+}$ induced by depolarizing stimuli in rat dorsal root ganglion neurons;

b) Andolast inhibits neuropeptide (CGRP) release from peripheral and central endings of primary sensory neurons;

c) Andolast inhibits the atropine-resistant eNANC contraction evoked in isolated guinea-pig bronchi by the application of electric stimuli (EFS). This contractile response is mediated by SP/NKA released from primary sensory neurons and acting on tachykinin receptors in the smooth muscle.

d) Charybdotoxin, a selective inhibitor of $K_{Ca}$, is able to revert the above-described Andolast activities.

METHODS

Experiments in Neurons in Culture

Dorsal root ganglia (DRG) were removed from 1-3 days old rats and dissociated into single cells according to well established procedures. Cells, plated on coated glass coverslips were loaded with Fura-2-AM-ester to detect relative intracellular calcium ($[Ca^{2+}]_i$) changes.

During the $Ca^{2+}$ fluorescence the cells were excited with electrical stimulation (10 Hz, 1 ms, 0.40 mA/cm$^2$ for 10 sec) twice with a resting period between each stimulation of 20 min. These experiments were performed in the presence or absence of 100 nM charybdotoxin.

Slices of Guinea Pig Airways and Rat Dorsal Spinal Cord:

Slices of guinea pig trachea and bronchi or of rat dorsal spinal cord were prepared and transferred to perfusion chambers and perfused. After an equilibration period, samples were collected before, during and after the delivery of an excitatory stimulus (KCl 80 mM). The effect of Andolast was compared with the effect of its vehicle. CGRP-like immunoreactivity (GCRP-LI) was measured by enzyme immunoassay (EIA).

In the rat dorsal spinal cord the experiments with Andolast were performed also in the presence of 100 nM charybdotoxin.

Isolated Guinea-pig Bronchi.

Guinea pig bronchial rings were mounted in organ baths. After an equilibration period the eNANC contractile response to EFS (5 Hz, 20 sec, 0.5 ms pulse width at 40 V) in the presence of atropine (1 µM) was studied. The effects of Andolast or its vehicle on the eNANC were studied in parallel experiments in the presence or absence of 100 nM charybdotoxin. The ability of Andolast to affect the direct bronchoconstrictor activity of SP was also studied.

RESULTS

Experiments in Neurons in Culture:

EFS induced an increase in $[Ca^{2+}]_i$, mobilization (59±8% of the response to ionomycin). All the cells that responded to EFS responded also to 0.1 µM capsaicin with an increase in $[Ca^{2+}]_i$, thus indicating that these were primary sensory neurons (polymodal nociceptor). Mobilization of $[Ca^{2+}]_i$ in response to ionomycin was similar after pre-treatment with Andolast (10 µM) or its vehicle. Pretreatment with Andolast diminished the response to EFS reduced in a concentration-dependent manner as compared to the effect of Andolast vehicle. The response to capsaicin was not affected by pretreatment with Andolast (10 µM). The inhibitory effect of Andolast was completely reversed by 100 nM charybdotoxin (ChTX). The data are illustrated in FIG. 1.

Slices of Rat Dorsal Spinal Cord and Guinea Pig Airways:

Both in slices of rat dorsal spinal cord and in slices of guinea pig airways Andolast (0.1-1 µM) did not cause any significant increase in the outflow of CGRP-LI.

In rat dorsal spinal cord, Andolast caused a concentration-dependent inhibition of the outflow of CGRP-LI induced by high K$^+$ medium. Maximum inhibition (48% of vehicle) was produced by Andolast (1 µM). This effect was completely abrogated by 100 nM charybdotoxin (FIG. 2A).

Figure 2B:
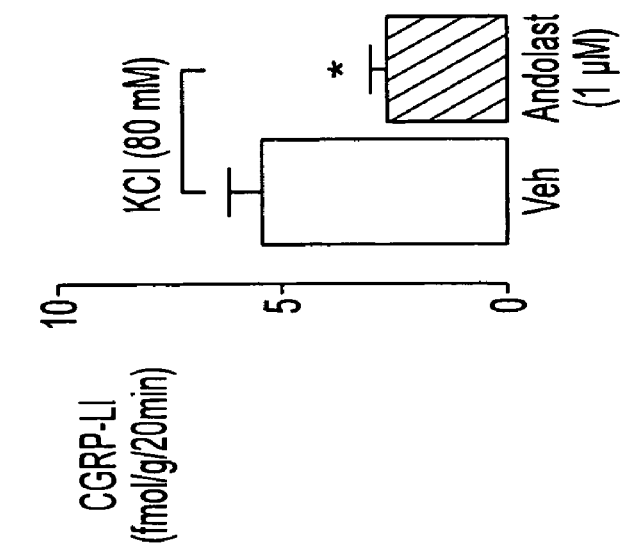
FIG. 2 illustrates the effect of Andolast and charybdotoxin (ChTX) on the outflow of CGRP evoked by high $K^+$ from slices of rat dorsal spinal cord (A), and from slices guinea pig airways (B).
Figure 2A:
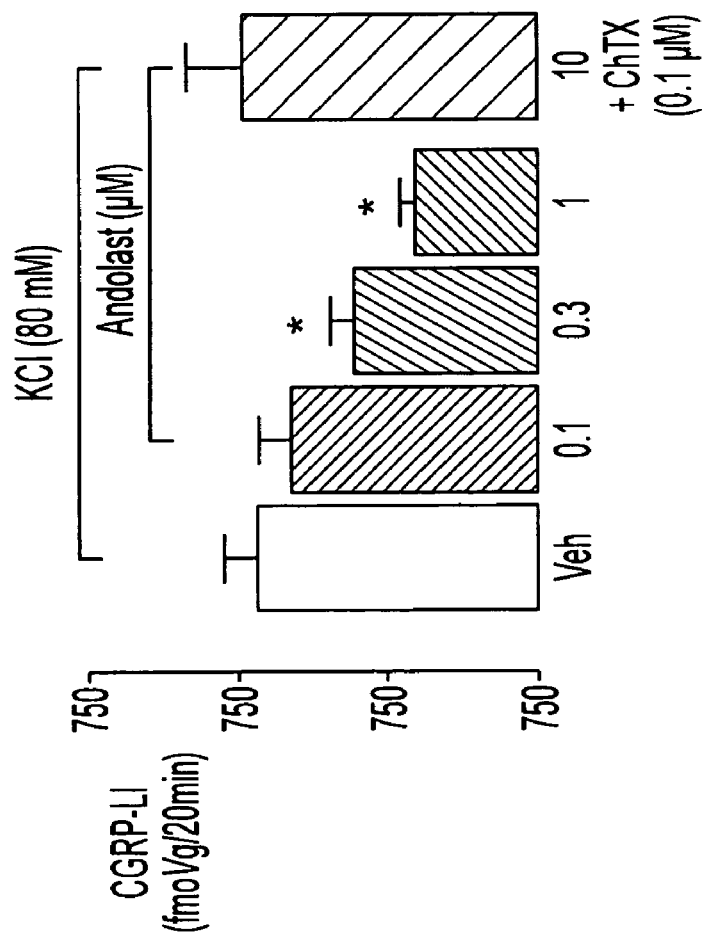

Also in slices of guinea pig airways Andolast (1 µM) caused a remarkable inhibition (67%) of the CGRP-LI outflow induced by high K+ medium (FIG. 2B).

Figure 3B:
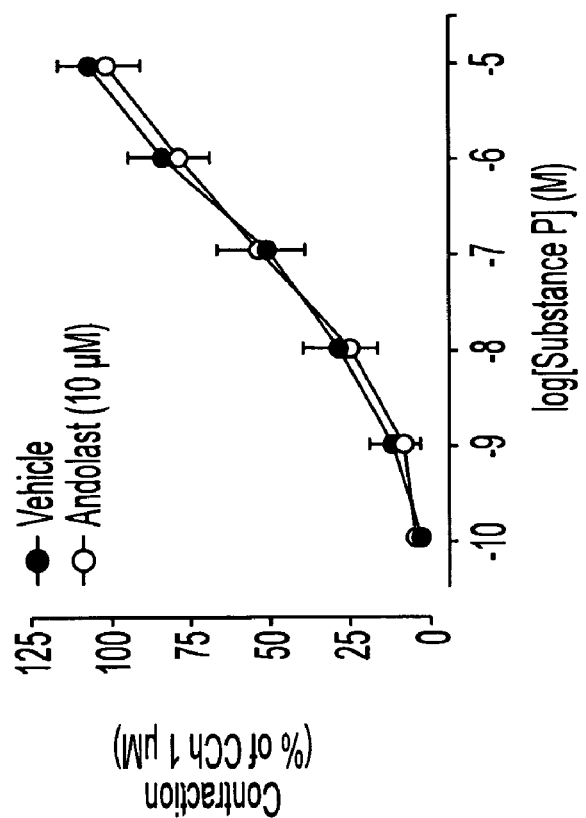
FIG. 3 illustrates the effect of Andolast and charybdotoxin (ChTX) on the contraction induced by electrical field stimulation (EFS, 5 Hz, 1 ms width, 10 V) and substance P in guinea pig isolated bronchial rings.
Figure 3A:
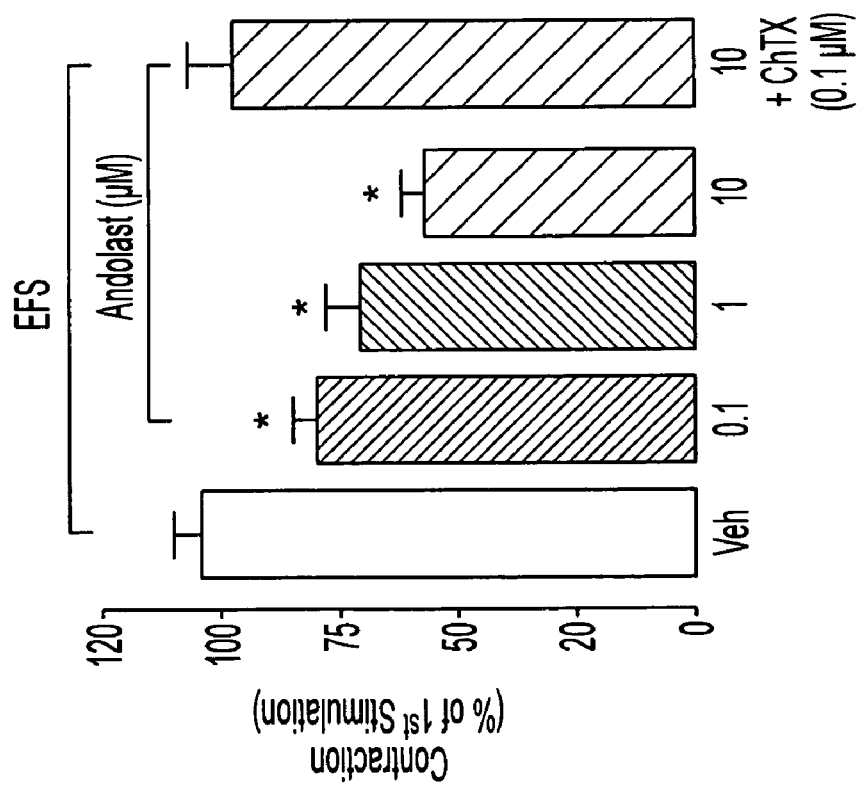

Isolated Guinea-pig Bronchi:

In the presence of atropine EFS caused a delayed contractile response in rings of guinea pig bronchi. Pretreatment with Andolast diminished dose-dependently the contractile response to EFS. Maximum inhibition (45%) was obtained with 10 µM Andolast. Andolast (10 µM) did not affect the contractile response to SP, thus indicating specificity. In the presence of the specific $BK_{Ca}$ inhibitor charybdotoxin (0.1 µM) the effect of Andolast was completely abrogated (FIG. 3).

CONCLUSIONS

Andolast causes inhibition of:
a) EFS-induced $Ca^{2+}$ mobilization in cultured primary sensory neurons;
b) Sensory neuropeptide release from slices of dorsal spinal cord of the rat, a tissue enriched of terminals of primary sensory neurons;
c) Sensory neuropeptide release from slices of guinea pig airways;
d) eNANC contraction produced by EFS in isolated guinea pig bronchi.

These findings indicate that Andolast exerts an inhibitory action on excitation of peripheral and central terminals of primary sensory neurons. The inhibitory effect of Andolast is directed toward a population of polymodal nociceptors that respond to capsaicin and release neuropeptides. These neurons are involved in the initiation of protective and proinflammatory reflexes and mediate neurogenic inflammatory responses. The findings obtained in the present study suggest that, at least part of the anti-inflammatory properties of Andolast in clinical experimental settings may be due to its ability to inhibit sensory neurons excitation.

Two observations indicate that the inhibitory action of Andolast on sensory neurons is specific. Andolast at the highest concentration used (10 µM) did not affect the increase in $[Ca^{2+}]_i$ produced by ionomycin in DRG neurons in culture. More importantly, Andolast did not produce any inhibitory effect on the contractile response produced by SP in isolated guinea pig bronchi. This observation indicates that Andolast does not act on tachykinin receptors and does not affect $Ca^{2+}$ influx into the smooth muscle cells, but most likely acts at a pre-junctional site of action on the sensory nerve terminal.

All these "anti-inflammatory" activities of Andolast were reversed by charybdotoxin.

Charybdotoxin is an inhibitor of $K_{Ca}$. Its ability to completely antagonize the protective effects of Andolast on neurogenic inflammation (i.e. $[Ca^{2+}]_i$ changes in rat DRG; CGRP release in rat dorsal spinal cord; and eNANC in isolated guinea-pig bronchial rings) supports the hypothesis that the molecular mechanism of action of Andolast is linked to the activation of specific $K_{Ca}$ channels involved in neurogenic inflammation.

Compounds used in the present invention are prepared according to the methods described in WO 90/09989.

The present invention includes within its scope the use of pharmaceutically acceptable salts of the compounds of formula (I) and particularly of formula (Ia). Representative salts utilized in pharmaceutical formulations of compounds of formula (I) and (Ia) include alkaline metal salts such as sodium, lithium or potassium, alkaline-earth salts such as magnesium and the like. Preferred pharmaceutical formulations for the compounds used in the present invention are those claimed in U.S. Pat. No. 5,976,576.

What is claimed is:

1. A method for the therapeutic treatment of Chronic Obstructive Pulmonary Disease comprising administering to a human patient in need thereof, an effective amount of the N-phenylbenzamide derivative of formula (I), or a pharmaceutically acceptable salt thereof

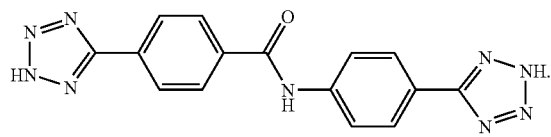

2. A method for the treatment of Pulmonary Emphysema comprising administering to an individual in need thereof an effective amount of a pharmaceutically active derivative of N-phenylbenzamide of formula (I), or of a pharmaceutically acceptable salt thereof

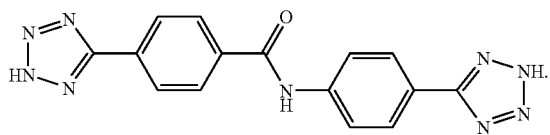

3. A method for the treatment of Chronic Bronchitis, comprising administering to an individual in need thereof an effective amount of a pharmaceutically active derivative of N-phenylbenzamide of formula (I), or of a pharmaceutically acceptable salt thereof

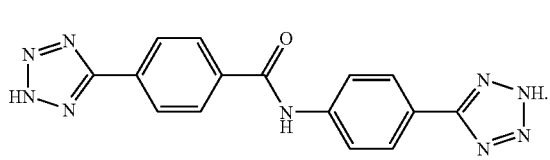

* * * * *